United States Patent [19]

Ono

[11] 4,150,120
[45] Apr. 17, 1979

[54] OPHTHALMIC

[75] Inventor: Hiroomi Ono, Chofu, Japan

[73] Assignee: Takeda Chemical Industries, Ltd., Japan

[21] Appl. No.: 865,722

[22] Filed: Dec. 29, 1977

[30] Foreign Application Priority Data

Jan. 5, 1977 [JP] Japan ........................................ 52-499

[51] Int. Cl.$^2$ ...................... A61K 37/00; C07C 103/52
[52] U.S. Cl. ............................. 424/177; 260/112.5 TR
[58] Field of Search ............... 260/112.5 TR; 424/177

[56] References Cited

U.S. PATENT DOCUMENTS

| 3,746,697 | 7/1973 | Folkers et al. | 260/112.5 TR |
| 3,932,623 | 1/1976 | Wilson | 424/177 |
| 4,059,692 | 11/1977 | Takahashi | 424/177 |

Primary Examiner—Delbert R. Phillips
Attorney, Agent, or Firm—Wenderoth, Lind & Ponack

[57] ABSTRACT

Eye diseases in mammals such as progressive cataract or conjunctivitis are effectively treated by administering to the mammals a thyroid stimulating hormone releasing hormone. The treatment effect is enhanced by the concomitant administration of the said hormone with an adrenocortica hormone.

12 Claims, No Drawings

OPHTHALMIC

The present invention relates to a therapeutic means for treating eye diseases.

While ocular opacity is an intractable eye disease in both human beings and animals, the gaining senile population has set off a rapid increase in the number of senile cataract (humans) which is characterized by an acquired opacification of the crystalline lens (hereinafter briefly referred to as lens) and by visual disturbances, with no effective remedies being available as yet. Aside from the congenital or stationary cataract which is beyond remedy, it has been attempted to arrest the progress of acquired progressive cataract by such treatments as the oral and ophthalmic administration of potassium iodide, the oral and parenteral administration of vitamin C, or the oral and parenteral administration of a detoxicant, for instance. More recently, the injection of a salivary glands hormone, the ophthalmic or parenteral administration of catalin, the ophthalmic administration of glutathione, etc. have been the common procedures. While the administration of such drugs may be expected to arrest the progress of progressive cataract in certain measures, it is reportedly difficult to obtain radical cures in cataractous cases.

Against the medical background described above, the present inventor discovered surprisingly that the administration of a thyroid stimulating hormone releasing hormone could lead to an effective improvement and a cure of the above-mentioned progressive opacification of the crystalline lens (progressive cataract), conjunctivitis and other eye diseases. This finding was followed by further studies which have resulted in the present invention.

Thus, the principal object of the present invention is to provide a method for the treatment of the eye diseases in mammals, which comprises administering to the mammals a thyroid stimulating hormone releasing hormone. Another object of the present invention is to provide an ophthalmic containing a thyroid stimulating hormone releasing hormone, which is usable in the above-mentioned method. Other objects will be made clear from the description and claims hereinafter.

The method of the present invention is applicable to the management of eye diseases in mammals (human beings, pets e.g. dogs and cats, domesticated animals e.g. horse and cattle, etc.) such as cataract, especially progressive cataract, and inflammatory eye diseases e.g. conjunctivitis, and can also be of use for maintenance care, i.e. the clarification of opacified eye balls.

The thyroid stimulating hormone releasing hormone may be natural or synthetic, and is typically exemplified by L-pyroglutamyl-L-histidyl-L-prolinamide (thyrotropin releasing hormone; hereinafter briefly referred to as TRH) and compounds having TRH-like activity, such as L-2-oxooxazolidine-4-carbonyl-L-histidyl-L-prolinamide, L-trans-5-methyl-2-oxooxazolidine-4-carbonyl-L-histidyl-L-prolinamide, L-2-oxothiazolidine-4-carbonyl-L-histidyl-L-prolinamide (German Patent Application No. P 2408324.7 laid open to public inspection on Aug. 29, 1974 as OLS 2408324) and so forth. These hormones may also be employed in the form of physiologically acceptable salts such as the acid addition salts of inorganic acids (e.g. hydrochloric acid, etc.) and of organic acids (acetic acid, tartaric acid, etc.). TRH tartrate is especially convenient for the administration.

The thyroid stimulating hormone releasing hormone is generally administered in an external dosage form such as an ophthalmic solution (including the form of a suspension), an ophthalmic ointment and the like. Such an external dosage form containing the thyroid stimulating hormone releasing hormone may be prepared by per se conventional techniques using suitable non-toxic carriers, diluents, preservatives, salts and/or boric acid for the preparation of ophthalmic solutions, ophthalmic ointments and the like, which are described, e.g. in pages 26, 27 and 35 of "The Pharmacopoeia of Japan", Eighth Edition (1971), Part I (English Edition).

Although the amount of the thyroid stimulating hormone releasing hormone to be contained in such an external ophthalmic varies with a type of the dosage forms and the particular thyroid stimulating hormone releasing hormone employed, it is generally advantageous that the ophthalmic contains the thyroid stimulating hormone releasing hormone in a concentration from about 0.001 to about 0.1 percent (hereinafter, all percents are by weight), especially from about 0.005 to about 0.01 percent, in terms of a free compound.

For the management of mild or moderate cases of progressive cataract or cases of acute conjunctivitis or of the opacification of the lens due to pyrexic diseases, a pronounced clarification of the lens can be expected by the administration in the external dosage form for about 5 to 90 consecutive days at the frequency of twice to six times a day. For the treatment of serious cases of progressive cataract which are more or less refractory to treatments using external preparations containing thyroid stimulating hormone releasing hormones, an adjunct therapy consisting of injections of the thyroid stimulating hormone releasing hormone is effective. The dosage for this injection depends upon the kind of mammals and the severity of the diseases, and it may generally be chosen from within the range of from about 20 to about 100 μg./kg. in terms of a free compound, when intravenously or intramuscularly administered.

The effect of the thyroid stimulating hormone releasing hormone on the eye diseases may be enhanced by the concomitant administration of this hormone with an adrenocortical hormone. The adrenocortical hormone may be natural or synthetic, thus being exemplified by 9α-fluorocortisone, 9α-fluorocortisol, prednisone, prednisolone, triamcinolone (9α-fluoro-16α-hydroxyprednisolone), midrol (6α-methylprednisolone), dexamethasone (9α-fluoro-16α-methylprednisolone), betamethasone (9α-fluoro-16β-methylprednisolone), paramethasone (6α-fluoro-16α-methylprednisolone), flumethasone (6α, 9α-difluoro-16α-methylprednisolone) and so forth. Among them, dexamethasone, betamethasone and flumethasone are conveniently employed. These hormones may be employed in the form of physiologically acceptable esters, such as phosphates, acetates, niconinates, etc. or physiologically acceptable salts of such esters such as alkali metal salts (e.g. sodium, potassium and lithium salts) and alkaline earth metal salts (e.g. calcium salts). When such an adrenocortical hormone is administered externally, advantageous use is made of an external ophthalmic such as an ophthalmic solution or ointment containing the hormone in a concentration from about 0.01 to about 0.1 percent in terms of a free compound. Such an external ophthalmic may be administered for consecutive days or intermittently, at the frequency of twice to six times per day. An external ophthalmic containing both the thyroid stimulating hormone releasing hormone and the adrenocortical hormone in the respective advantageous concentrations may be prepared by per se conventional techniques mentioned above.

The ophthalmic of the present invention may, if desired, contain other and conventional ophthalmic ingredients such as antibiotics, vitamins, amino acids and so forth.

According to the present invention, eye diseases such as progressive cataract and conjunctivitis can be effectively treated without any undesirable side-effect and, therefore, the present invention highly contributes to the ophthalmological field.

The following Examples are merely for illustrative purposes and are not to be construed as limitations of the present invention.

Throughout the foregoing description as well as in the following Examples and Claims, "μg.", "mg.", "kg." and "ml." respectively refer to "microgram(s)", "milligram(s)", "kilogram(s)" and "milliliter(s)", and percents are by weight.

EXAMPLE 1

Treatment of cases of progressive cataract (dogs) by the ophthalmic instillation of a 0.01% (in terms of free TRH) aqueous solution of TRH tartrate.

Heretofore, attempts have been made to arrest the progress of senile cataract by the ophthalmic instillation of catalin. The present cases are catalin-refractory dogs as treated with ophthalmic instillations of TRH alone.

Case 1

(Species of dog) Kwantung Dog, male
(Age & body weight) 11 years, 7.5 kg.
(Diagnosis) Progressive total cataract (bilateral)
(Symptoms and treatment)

The onset of cataractous symptoms occurred around February, 1976. Kept indoors, the dog suffered visual disturbances, the severity of which was such that the dog bumped against the tables, chairs and kitchen corners. With this progress of the disease, instillations of catalin were made without avail. Starting on the 21st day of May, a 0.01% aqueous solution of TRH tartrate was given at the rate of 2 instillations daily for 3 consecutive days. The result was apparently satisfactory but the medication was discontinued. The dosing was resumed for 4 consecutive days from the 10th of June. As a result, the apparent opacity of the eye balls started being mitigated from the third day and, on the fourth day, there was a recovery of visual acuity, with no disturbance in gait being observed any longer. Therefore, the case was judged to have been cured but further treated with similar instillations for 3 days.

After each instillation, apparently due to an irritation to the conjunctiva, the dog closed the lids for a while, followed by several blinkings. However, it was considered that this was not tantamount to a pain to the dog.

Now, as of the end of October, no abnormal development is seen after a substantial recovery (a slight degree of opacity remains in the lens and the dog is in full vigor), with no signs of relapse.

Case 2

(Species of dog) Japanese Spaniel, male
(Age & weight) 9 years, 4.8 kg.
(Diagnosis) Progressive total cataract (bilateral)
(Symptoms and treatment)

In early winter of 1975, the dog was found to start developing a cataract and, by April, 1976, one of its eyes was found to have turned almost opaque, the dog becoming more meticulous in walking and alert. A therapy consisting of ophthalmic instillations of catalin failed to bring about improvements and the owner of the animal throught that his pet was in a desperate condition.

Starting on the 20th day of July, ophthalmic instillations of a 0.01% aqueous solution of TRH tartrate were given twice daily on a continuous basis. As a result, on the 7th day, a certain response was noted. By the 10th day, the eye balls had shown a marked clarification, the dilated capillary vessels exposed on the eye balls having been deflated and the dog having recovered its visual acuity excepting a slight opacity of the lens. Accordingly, the case was judged to have been cured. As of the end of October, there were no signs of a relapse.

In the following seven cases, the effects of therapy were promoted because the overflows of the medication were prevented by pressing the upper and lower eye lids after the instillation and it was generally found that, in the case of a 0.01% aqueous solution, 3 instillations a day elicited responses on the third day and resulted in cures on the 5th day.

In the serious case of progressive bilateral cataract (Case No. 7), the application of TRH.corson injection [mixed intramuscular injection of 0.5 ml. of 0.125 mg. TRH tartrate and 1 ml. of 1 mg. dexamethasone(synthetic adrenocortical hormone)] as an adjunct to the instillation of the ophthalmic solution of TRH resulted in an improved effect.

Cases of progressive cataract as treated by the opthalmic installation of 0.01% TRH tartrate

| Case No. | Diagnosis | Species and sex of dog | Age & weight | Medication and results | Evaluation | Relapse* |
|---|---|---|---|---|---|---|
| 3 | Central cataract (bilateral) | Kwantung Dog, female | 9 years 4.8 kg. | 3 instillations daily; lens clarified on 3rd day, with cure occurring on 7th day | ++** | None |
| 4 | Total cataract (bilateral) | Japanese Spaniel, male | 8 years 4.2 kg. | 3 instillations daily; lens clarified on 3rd day, with cure occurring on 5th day | ++ | None |
| 5 | Total cataract (bilateral) | Japanese Spaniel, male | 7 years 3.8 kg. | 3 instillations daily; lens clarified on 3rd day, with cure occurring on 5th day | +++*** | None |
| 6 | Central cataract | Pekinese, | 8 years | 3 instillations | ++ | None |

-continued

Cases of progressive cataract as treated by the opthalmic installation of 0.01% TRH tartrate

| Case No. | Diagnosis | Species and sex of dog | Age & weight | Medication and results | Evaluation | Relapse* |
|---|---|---|---|---|---|---|
| | (bilateral) | famlae | 6.5 kg. | daily; lens clarified on 3rd day, with cure occurring on 5th day | | |
| 7 | Total cataract (bilateral) | Japanese Shiba, female | 7 years 8 kg. | 3 installations daily for 4 days; TRH.corson injections on 1st and 3rd days; clarification and cure occurred on 4th day and 5th day, respectively | ++ | None |
| 8 | Total cataract (bilateral) | Dachshund, female | 9 years 6.5 kg. | 3 installations daily; lens clarified on 2nd day, with cure occurring on 5th day | ++ | None |
| 9 | Transient central cataract due to traumatic corneitis (left eye) | Pekinese, female | 2 years 4.3 kg. | 2 installations daily; severe lens opacity cleared away on 3rd day, cure occurring on 4th day | +++ | follow-up |

Note:
Relapse* diagnosed after 3 months
++**(almost cured) traces of lens opacity, with visual acuity regained
+++*** completely cured

EXAMPLE 2

Cases of acute conjunctivitis (dogs) as treated by the ophthalmic instillation of a 0.01% (in terms of free TRH) aqueous solution of TRH tartrate.

It is common practice to employ, as therapeutic agents for the treatment of conjunctivitis and other inflammatory eye diseases, ophthalmic ointments or solutions of antiinflammatory drugs such as synthetic adrenocortical hormones or/and antibiotics.

The following examples illustrate the treatment of a case of acute catarrhal conjunctivitis and a case of drug-induced acute conjunctivitis, by ophthalmic instillation of TRH alone.

Case 1

(Species of dog) Maltese, male
(Age & weight) 6 months, 4.3 kg.
(Diagnosis) Acute catarrhal conjunctivitis
(Symptoms) The dog rubbed the eyes with its paw, being nervous.

The appetite, defecation, and temperature normal; conjunctival injection; resistance and pain on ocular examination. Tears containing a viscous fluid, catarrhal.
(Treatment)

Three instillations of a 0.01% aqueous solution of TRH tartrate, given every other day. The examination on the 7th day after the start of treatment revealed neither a hyperemia nor overflowing tears. The case was judged to have been cured.

Case 2

(Species of dog) Labrador Retriever, male
(Age & weight) 2 years, 18 kg.
(Diagnosis) Acute conjunctivitis due to irritation by drug (insecticide)
(Symptoms) Vigor and temperature normal, the sclera (white area) was injected, red and dilated.
(Treatment) 2 instillations of a 0.01% aqueous solution of TRH tartrate, given every other day.

When the third instillation was contemplated, the hyperemia had disappeared and the slightly dilated eye balls had become normal. The case was indead to have been cured.

EXAMPLE 3

Case 1

(Species of dog) Japanese Spaniel, female
(Age) 7 years
(Diagnosis) Total cataract in transitional stage from immature cataract to mature cataract
(Symptoms) The pupillary reflex was positive but dull, and, in the pupillary area, the lens had turned opaque to the extent of genuine white, with the opacity making it impossible to inspect the fundusoculi.
(Treatment) Ophthalmic instillations of a 0.01% (in terms of free TRH) aqueous solution of TRH tartrate were given 4 to 5 times daily from Feb. 2, 1977.

On February 28, the pupillary reflex was found to be normal, the pupillary area had a reduced opacity, and with the dilation of pupil it was found that the opacity had been thinned permitting a fundusoculi inspection.

On March 10 it was found through a visual examination that the clarity of the cortex of lens had been improved.

No side effect was noted at the times of instillation.

Case 2

(Species of dog) Japanese Dog, female
(Age) 12 years
(Diagnosis) Senile cataract in a transitional stage from incipient cataract to immature cataract.
(Treatment) Starting on Feb. 28, 1977 opthalmic instillations of a 0.01% aqueous solution of free TRH were given 3 times a day.

On April 23, the lens cortex of the right eye was remarkably clear and the circumstances of lens in the left eye could be delineated.

No side effect was observed during the instillation period.

Case 3

(Species of dog) Cocker Spaniel, female
(Age) 3 years and 6 months
(Diagnosis)
 Left eye: Immature cortical cataract and corneitis
 Right eye: Immature cortical cataract
(Symptoms)
 Left eye: The lens had bluish-white opacities, the conjunctiva revealed a ciliary congestion and the cornea showed a pannus, with a dull light response and a poor dilation of the pupil.
 Right eye: The lens showed bluish-white opacities except its upper margin but the pupillary reflex was satisfactory.
(Treatment) Starting on Aug. 13, 1977 the left eye was treated by the ophthalmic instillations of a 0.01% (in terms of free TRH) aqueous solution of TRH tartrate, a 0.02% aqueous solution of dexamethasone and a 0.05% aqueous solution of flavine-adenine dinucleotide at a frequency of 5 to 6 times daily. The right eye was treated simultaneously with the aqueous solution of TRH tartrate alone.

On August 20, in the left eye the pannus had disappeared, the pupillary reflex and dilation were satisfactory but the ciliary congestion persisted. The right eye showed increased clarity in the upper margin of the lens. For both eyes the ophthalmic instillations of the TRH tartrate solution and the dexamethasone solution twice daily were indicated.

On September 2, both eyes had only thinned opacities all over the lens and the dog bumped less frequently. The ophthalmic instillation of the TRH tartrate solution alone was indicated.

On September 25, both eyes showed significantly increased clarity, the improvements being such that the fundus was sufficiently visible.

EXAMPLE 4

(1) By a procedure per se conventional, an ophthalmic solution is produced which contains 0.005% (in terms of free TRH) of TRH tartrate and has the following composition:

| TRH tartrate | 0.005% (in terms of free TRH) |
|---|---|
| Sodium chloride | 0.55% |
| Potassium chloride | 0.16% |
| Sodium carbonate | 0.06% |
| Disodium hydrogenphosphate | 0.18% |
| Boric acid | 1.20% |
| Methyl-cellulose | 0.21% |
| Benzalconium chloride | 0.005% |

(2) Under aseptic conditions, 0.05 g. (in terms of free TRH) of TRH tartrate is evenly dispersed into 10 g. of liquid paraffin and, then, a sufficient amount of white petrolatum, melted at about 60° C., is added to the dispersion to make a total of 100 g. The mixture is stirred to homogeniety and cooled, whereby a TRH tartrate-containing ophthalmic ointment is obtained.

EXAMPLE 5

(1) An ophthalmic solution having the following composition is produced by a per se conventional procedure:

| TRH tartrate | 0.01% (in terms of free TRH) |
|---|---|
| Boric acid | 0.5% |
| Sodium chloride | 0.6% |
| Sodium acetate | 0.2% |
| Methyl para-hydroxybenzoate | 0.026% |
| Propyl para-hydroxybenzoate | 0.014% |
| Chlorobutanol | 0.2% |
| Adjusted to pH 5.6 with hydrochloric acid. | |

(2) Under aseptic conditions, to 0.075 g. of TRH tartrate (0.05 g. in terms of free TRH) in a glass mortar there is added 5 g. of liquid paraffin and the mixture is ground. Into the mortar is added 95 g. of white petrolatum little by little under stirring, and the mixture is stirred to homogeniety, whereby a TRH tartrate-containing ophthalmic ointment is produced.

What is claimed is:

1. A method for treating an eye disease in a mammal, which comprises administering to the mammal an effective amount in an external dosage form of a thyroid stimulating hormone releasing hormone.
2. A method as claimed in claim 1, wherein the eye disease is cataract or an inflammatory eye disease.
3. A method as claimed in claim 2, wherein the cataract is progressive cataract.
4. A method as claimed in claim 2, wherein the inflammatory eye disease is conjunctivitis.
5. A method as claimed in claim 1, wherein the thyroid stimulating hormone releasing hormone is in the form of a physiologically acceptable salt.
6. A method as claimed in claim 1, wherein the thyroid stimulating hormone releasing hormone is L-pyroglutamyl-L-histidyl-L-prolinamide or its physiologically acceptable salt.
7. A method as claimed in claim 6, wherein the physiologically acceptable salt is tartrate.
8. A method as claimed in claim 1, wherein the external dosage form is an ophthalmic solution or an ophthalmic ointment.
9. A method as claimed in claim 8, wherein the external dosage form contains the thyroid stimulating hormone releasing hormone in a concentration from about 0.001 to about 0.1 percent.
10. A method as claimed in claim 1, wherein the thyroid stimulating hormone releasing hormone is administered in conjunction with an adrenocortical hormone.
11. A method as claimed in claim 10, wherein the adrenocortical hormone is in the form of a physiologically acceptable ester or its salt.
12. A method as claimed in claim 10, wherein the adrenocortical hormone is dexamethasone or betamethasone.

* * * * *